(12) United States Patent
Kitamura et al.

(10) Patent No.: US 6,204,362 B1
(45) Date of Patent: Mar. 20, 2001

(54) METHOD OF PURIFYING WHEY OF LACTIC ACID FERMENTATION BY ELECTRODIALYSIS

(75) Inventors: Shuji Kitamura, Tokyo; Takashi Ueyama, Kanagawa-ken, both of (JP)

(73) Assignee: Calpis Co., Ltd., Tokyo (JP)

( * ) Notice: Subject to any disclaimer, the term of this patent is extended or adjusted under 35 U.S.C. 154(b) by 0 days.

(21) Appl. No.: 09/231,448

(22) Filed: Jan. 14, 1999

(30) Foreign Application Priority Data

Jan. 11, 1999 (JP) .................................................. 11-004131

(51) Int. Cl.$^7$ ....................................................... C07K 1/24
(52) U.S. Cl. ........................... 530/344; 530/421; 530/414; 530/417
(58) Field of Search .................................... 530/412, 414, 530/417, 344

(56) References Cited

U.S. PATENT DOCUMENTS

| | | | |
|---|---|---|---|
| 4,110,175 | * 8/1978 | Ahlgren et al. | 204/180 P |
| 4,227,981 | * 10/1980 | Williams et al. | 204/180 P |
| 4,781,809 | * 11/1988 | Falcone, Jr. | 204/182.4 |
| 4,906,616 | 3/1990 | Gilchrist et al. | 514/21 |
| 5,064,538 | 11/1991 | Boeteng | 210/638 |
| 5,681,728 | * 10/1997 | Miao | 435/136 |
| 5,780,438 | 7/1998 | Gilchrist et al. | 514/21 |

FOREIGN PATENT DOCUMENTS

| | | |
|---|---|---|
| 04282398 | * 10/1992 | (JP) . |
| 04282400 | * 10/1992 | (JP) . |
| 08269088 | * 10/1996 | (JP) . |

OTHER PUBLICATIONS

Japanese Patent Laid–Open Publication Shou 52–134050 Nov. 1977 with abstract.
Japanese Patent Laid–Open Publication Shou 64–80407 with abstract Mar. 1989.
Japanese Patent Laid–Open Publication Hei2–63527 with abstract Mar. 1990.

* cited by examiner

Primary Examiner—Jon P. Weber
(74) Attorney, Agent, or Firm—Darby & Darby

(57) ABSTRACT

In a method of purifying whey separated from lactic acid fermentation liquid by electrodialysis wherein said whey contains angiotensin-converting enzyme inhibiting peptides, the improvement which comprises using an anion exchange membrane having a permeability of diffusion coefficient in the range of 3.0 to $9.0 \times 10^{-6}$ cm/sec. An anion exchange membrane having a permeability of diffusion coefficient in the range of 5.0 to $7.0 \times 10^{-6}$ cm/sec. is more efficiently used. The product is particularly suited to produce granules and tablets.

6 Claims, No Drawings

SEQUENCE LISTING

<160> NUMBER OF SEQ ID NOS: 1

<210> SEQ ID NO 1
<211> LENGTH: 10
<212> TYPE: PRT
<213> ORGANISM: Human

<400> SEQUENCE: 1

```
Asp Arg Val Tyr Ile His Pro Phe His Leu
1               5                   10
```

METHOD OF PURIFYING WHEY OF LACTIC ACID FERMENTATION BY ELECTRODIALYSIS

BACKGROUND OF THE INVENTION

The present invention relates to a method of purifying whey separated from lactic acid fermentation liquid by electrodialysis. The whey contains angiotensin-converting enzyme inhibiting peptides. The peptides obtained in the purified whey according to the present invention can be used for anti-high blood pressure agent or foods, when the whey is further treated for oral administration.

The angiotensin-converting enzyme, hereinafter referred to as ACE, is mainly present in lungs and vascular endothelial cells, and acts on angiotensin I (Asp-Arg-Val-Tyr-Ile-His-Pro-Phe-His-Leu SEQ ID No:1) to remove a dipeptide (His-Leu) at its c-terminal and to form angiotensin II, which has a strong blood pressure increasing activity. The ACE also has an ability to decompose and to inactivate bradykinin which decreases blood pressure. Thus, the ACE acts to increase blood pressure by producing angiotensin II on the one hand, while decomposing bradykinin to increase blood pressure. Accordingly, when the angiotensin-converting enzyme is inhibited, high blood pressure could decrease, and many drugs which contain the angiotensin-converting enzyme inhibitor have been developed and used for anti-high blood pressure.

Certain peptides were recently found to be useful, being as low in toxicity and highly safe anti-high blood pressure agents, and natural and synthetic peptides are reported to be possible anti-high blood pressure drugs (Japanese Patent Publication No.120,225/1991). It is also known that peptides containing Ile-Pro-Pro (hereinafter referred to as IPP) or Val-Pro-Pro (hereinafter referred to as VPP) as its basic peptide structure have ACE inhibiting properties, and that these peptides can be produced in large amounts by culturing certain lactic acid bacteria, or lactic acid bacteria and yeast (Japanese patents Nos.2,782,142 and 2,782,153). Drugs or foods consisting of the peptides are proposed to be highly safe and useful in a small amount for decreasing high blood pressure in forms of oral administration, when the cultured liquid is treated for purification and separation.

It may be possible to use the fermentation liquid as obtained in accordance with the processes described in the above patents as the ACE-inhibiting drugs or foods containing the ACE inhibiting peptides (hereinafter referred to as ACEI peptides). However, it may have poor palatability for oral intake, and is not appropriate to drink without further purification processes, because they contain lactic acid and some other substances to some extent. Accordingly, it is desirable to remove substances other than the ACEI peptides from the liquid. Drugs or foods in a dry form including the peptides are in more concentrated form than the liquid are more useful. Proteins and the ACEI peptides having IPP or VPP as its basic peptide structure, which are produced by culturing lactic acid bacteria or lactic acid bacteria and yeast are partly hydrolyzed to form IPP and VPP in the cultured broth.

BRIEF DESCRIPTION OF THE INVENTION

The fermentation liquid is subjected to treatments for solid-liquid separation, including centrifugation and filtration to obtain whey as a supernatant, which contains a major portion of the ACEI peptides. The acids and other impurities in the whey may be removed by subjecting the whey to one or a combination of the following treatments including electrodialysis, a treatment with ion exchange resins, hollow fiber membrane dialysis, reverse osmosis treatment, and hydrophobic column chromatography. The purified whey is converted to dry matter containing ACEI peptides.

Electrodialysis is generally considered to be one of the most advantageous techniques to purify the whey, however, generally known dialysis has disadvantages in that it took a long period for the dialysis, because of slow movement of ions due to polarization or fouling. Another disadvantage of electrodialysis is low efficiency in recovering the end product ACEI peptides, because proteins and other compounds having large molecule sizes resolved in the whey may decrease permeability of acids, water, and other ions through the ion exchange membrane. On the other hand, ACEI peptides, such as IPP and VPP, having small molecular sizes easily penetrate through the membrane.

We have now found that when an anion exchange membrane having a permeability of diffusion coefficient in a range of 3.0 to $9.0 \times 10^{-6}$ cm/sec., more preferably in a range of from 5.0 through $7.0 \times 10^{-6}$ cm/sec., is used for purification and concentration of the whey, which is obtained from lactic acid fermentation liquid by separation, and contains ACEI peptides, the lactic acid and other ions are smoothly removed, and the ACEI peptides can be recovered in very high yield for a very short period of treatment; nevertheless, the membrane is called loose-type membrane and has rather large holes, through which charged substances having large molecular weights easily penetrate.

Accordingly, there is provided a method of purifying whey separated from lactic acid fermentation liquid containing ACEI peptides by electrodialysis, which comprises using an anion exchange membrane having a permeability of diffusion coefficient in a range of 3.0 to $9.0 \times 10^{-6}$ cm/sec., and more preferably in the range of 5.0 through $7.0 \times 10^{-6}$ cm/sec. in the dialysis.

It is an aspect of the present invention to provide an efficient method of electrodialysis to remove lactic acid and ions other than ACEI peptides from whey.

It is another aspect of the present invention to provide a method of purifying whey by electrodialysis to remove lactic acid and ions other than ACEI peptides in a short period of time.

DETAILED DESCRIPTION OF THE INVENTION

The lactic acid fermentation liquid containing ACEI peptides can be obtained by culturing lactic acid bacteria, or lactic acid bacteria and yeast in accordance with the description in Japanese Patents Nos. 2,782,142 and 2,782,153. Whey can be obtained from the fermentation liquid as supernatant by solid-liquid separation, including centrifugation, filtration or decantation of the liquid. Whey thus obtained contain large amounts of ACEI peptides as well as acids, other ions and proteins, and subjected to electrodialysis for purification. If desired, the solutions may be partly concentrated under diminished pressure before subjecting to dialysis.

In the method of purifying the whey by electrodialysis according to the present invention, an anion exchange membrane having a permeability of diffusion coefficient in the range of 3.0 to $9.0 \times 10^{-6}$ cm/sec., and more preferably, in the range of 5.0 to $7.0 \times 10^{-6}$ cm/sec. is used. The diffusion coefficient was determined by the following processes; 0.5 normal sodium chloride solution-membrane-3 normal sodium chloride solution are stirred in a vessel, differences in the concentration of the sodium chloride is measured, and diffusion coefficient of the used membrane was determined by the formula of:

Diffusion coefficient(cm/sec.)=transferred amount of sodium chloride(mol/sec.)×area of membrane(cm$^2$)×ΔC(mol/cc)

Cation permeable ion exchange membrane which can be used in the present invention may not have any restrictions, and suitable membranes may include those having a permeability of diffusion coefficient in the range of 3.0 to 5.0×10$^{-6}$ cm/sec., and those in the range of 4.0 to 6.0×10$^{-6}$ cm/sec, and other membranes giving similar results may be used.

There are no more operating conditions to be added to conventional electrodialysis particularly according to the present invention, generally known electrodialysis units can be used, and the current applied to the electrodes is controlled to maximize current efficiency. The rate of conductivity of the whey to the current density may be that generally used, and the dialysis is performed at ambient temperatures up to about 50° C., for 3 to 10 hours. During dialysis, acids including lactic acids, and other charged substances will be removed from the whey into a diffusate, while ACEI peptides remain in a dialyzate. According to the present invention, the dialysis is completed for a much shorter period with a higher yield of ACE inhibitor than that where anion exchange membrane having an outside range of the diffusion coefficient of the present invention is used. For medicinal applications, the purified whey solution may be dried by conventional drying methods.

EXAMPLE 1

112 Kilograms lactic acid fermentation liquid was prepared in accordance with Japanese Patent No. 2,782,153, and the liquid was subjected to a centrifugation with 10,000 r.p.m. for 5 minutes. The supernatant (whey solution) contained 2.1 mg/100 g of IPP, and 3.9 mg/100 g of VPP.

In the present invention, ACEI activities of IPP are 1.7 times that of VPP, and accordingly, the amounts of ACEI peptides are defined as combined amounts of IPP and VPP calculated by the following formula:

Amount of ACEI peptides (as VPP amount)=amount of IPP(mg/100 g)×1.7+amount of VPP(mg/100 g)

The supernatant obtained above was distilled under vacuum in a long plate type evaporator, "Super-Long Plate Evaporator RET-100," manufactured by Hisaka Co., Ltd., Japan, to a total volume of one seventh (1/7), and a concentrated whey obtained. It had properties of pH 3.0, and contained 37.67% (W/W) saccharide, 62.2% water, 13.8% acid and 52.4 mg/100 g ACEI peptides.

3 Kg of the concentrated whey solution was subjected to a electrodialysis by using a unit of TS-2-10 type dialyzer, manufactured by Tokuyama Co., Ltd., Japan. The unit was assembled with 10 pairs of an anion exchange membrane "Neosepta AMX" having a permeability of diffusion coefficient of 6.0×10$^{-6}$ cm/sec. and having an effective surface area of 2 dM$^2$ per sheet of membrane, manufactured by Tokuyama Co,.Ltd., Japan, and a cation exchange membrane "Neosepta CMX" having a permeability of diffusion coefficient of 5.0×10$^{-6}$ cm/sec. and having an effective surface area of 2 dM$^2$ per sheet of membrane, manufactured by Tokuyama Co,. Ltd., Japan. The voltage applied to the vessel was 14.2 volts, the initial current was 2.94 A, the final current was 1.41 A. The total current applied was 15.5 AH at 15 to 30° C. for 620 minutes. Results obtained are shown in Table 1.

TABLE 1

|  | Initial Solution | Final Solution |
| --- | --- | --- |
| Amount of Solution (kg) | 3.0 | 1.63 |
| Acid (W/W %) | 13.8 | 0.94 |
| Rate of Concentration (%) ※1 | — | 184 |
| Removal rate of solid matter (%) ※2 | — | 60 |
| Amount of ACEI peptides contained (mg/100 g) | 52.4 | 80.9 |
| ACE inhibiting activity contained (unit/gram) | 0.63 | 0.97 |

Note
※1 Rate of concentration = initial solution fed/final solution
※2 Removal rate of solid matter (%) = (initial solid matter − final solid matter)/initial solid matter × 100

EXAMPLE 2

Experiments similar to Example 1 were repeated by using anion exchange membranes having various diffusion coefficients as indicated in Table 2. Results obtained are shown in Table 2.

TABLE 2

| Diffusion coefficient (10$^{-6}$ cm/sec) | 1 | 3 | 5 | 7 | 9 | 11 |
| --- | --- | --- | --- | --- | --- | --- |
| Initial solution fed (kg) | 3 | 3 | 3 | 3 | 3 | 3 |
| Final solution obtained (kg) | 2.3 | 2.07 | 1.7 | 1.7 | 1.5 | 1.4 |
| Period treated (minutes) | 760 | 700 | 620 | 620 | 580 | 530 |
| Initial acid (w/w %) | 13.8 | 13.8 | 13.8 | 13.8 | 13.8 | 13.8 |
| Final acid (w/w %) | 0.93 | 0.94 | 0.94 | 0.95 | 0.93 | 0.94 |
| Rate of Concentration (%) | 130 | 145 | 176 | 176 | 200 | 214 |
| Removal rate of solid matter (%) | 38 | 50 | 59 | 59 | 64 | 69 |
| ACEI peptides (mg/100 g) |  |  |  |  |  |  |
| Initial solution | 52.4 | 52.4 | 52.4 | 52.4 | 52.4 | 52.4 |
| Final solution | 65.2 | 65.3 | 80.8 | 80.7 | 66.4 | 56.8 |
| ACEI activity (unit/g solid) |  |  |  |  |  |  |
| Initial solution | 1.6 | 1.6 | 1.6 | 1.6 | 1.6 | 1.6 |
| Final solution | 2.5 | 2.8 | 3.5 | 3.5 | 2.9 | 2.7 |

The results show that when an anion exchange membrane having a permeability of diffusion coefficient in the range of 3.0 to 9.0×10$^{-6}$ cm/sec., and more preferably, in the range of 5.0 to 7.0×10$^{-6}$ cm/sec. is used, acids including lactic acid, other ions and water were efficiently removed for a short period of time, while ACEI activities remained in the concentrated dialyzate at high yields.

What we claim is:

1. In a method of purifying whey separated from lactic acid fermentation liquid by electrodialysis wherein said whey contains angiotensin-converting enzyme inhibiting peptides, the improvement which comprises carrying out said method using an anion exchange membrane having a permeability of diffusion coefficient in the range of 3.0 to $9.0 \times 10^{-6}$ cm/sec, wherein the diffusion coefficient of the anion exchange membrane is determined by:

(a) maintaining a first 0.5 normal sodium chloride solution on one side of the anion exchange membrane in a vessel, and maintaining a second 3.0 normal sodium chloride solution on the other side of the membrane in said vessel;

(b) stirring the first and second sodium chloride solutions;

(c) measuring the differences in the concentration of the two sodium chloride solutions, and (d) calculating the diffusion coefficient by applying the formula:

Diffusion coefficient (cm/sec)=transferred amount of sodium chloride(mol/sec)*area of membrane($cm^2$)*$\Delta C$(mol/cc).

2. The method according to claim 1, wherein said anion exchange membrane has a permeability of diffusion coefficient in the range of 5.0 to $7.0 \times 10^{-6}$ cm/sec.

3. The method according to claim 1, wherein said whey is obtained from fermentation liquid as a supernatant by solid-liquid separation before electrodialysis.

4. The method according to claim 1, wherein said whey is partly concentrated under diminished pressure before electrodialysis.

5. The method according to claim 2, wherein said whey is obtained from fermentation liquid as a supernatant by solid-liquid separation before electrodialysis.

6. The method according to claim 2, wherein said whey is partly concentrated under diminished pressure before electrodialysis.

* * * * *